(12) United States Patent
Tanemura et al.

(10) Patent No.: US 9,089,550 B2
(45) Date of Patent: Jul. 28, 2015

(54) COMBINED ISLET TRANSPLANTATION USING PANCREATIC ISLETS AND ADIPOSE TISSUE DERIVED STEM CELLS

(75) Inventors: Masahiro Tanemura, Suita (JP); Yoshiaki Omura, Suita (JP); Hiroaki Nagano, Suita (JP); Masaki Mori, Suita (JP); Yuichiro Doki, Suita (JP); Toshinori Ito, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 13/814,489

(22) PCT Filed: Aug. 5, 2011

(86) PCT No.: PCT/JP2011/067992
§ 371 (c)(1),
(2), (4) Date: Mar. 13, 2013

(87) PCT Pub. No.: WO2012/018127
PCT Pub. Date: Feb. 9, 2012

(65) Prior Publication Data
US 2013/0171114 A1    Jul. 4, 2013

(30) Foreign Application Priority Data
Aug. 6, 2010 (JP) ................ 2010-177993

(51) Int. Cl.
*A61K 35/39*    (2015.01)
*C12N 5/071*    (2010.01)
*A61K 35/28*    (2015.01)

(52) U.S. Cl.
CPC .......... *A61K 35/39* (2013.01); *A61K 35/28* (2013.01); *C12N 5/0676* (2013.01); *C12N 2502/1382* (2013.01)

(58) Field of Classification Search
None
See application file for complete search history.

(56) References Cited

FOREIGN PATENT DOCUMENTS

| JP | 2007-525422 | 9/2007 |
|---|---|---|
| JP | 2008-500809 | 1/2008 |
| WO | 2004/074457 | 9/2004 |
| WO | 2005/086860 | 9/2005 |
| WO | 2008/150368 | 12/2008 |

OTHER PUBLICATIONS

Federal Register, vol. 79, No. 241, Tuesday, Dec. 16, 2014, pp. 74618-74633, accessed from http://www.gpo.gov/fdsys/pkg/FR-2014-12-16/pdf/2014-29414.pdf on Dec. 16, 2014.*

(Continued)

*Primary Examiner* — Ralph Gitomer
*Assistant Examiner* — Trent Clarke
(74) *Attorney, Agent, or Firm* — Roylance, Abrams, Berdo & Goodman, L.L.P.

(57) ABSTRACT

An object of the present invention is to provide a pancreatic islet transplantation technique that enables increase of graft survival rate of pancreatic islets after pancreatic islet transplantation, to maintain survival of pancreatic islets, and to reduce the number of transplanted pancreatic islets required for normalizing blood glucose level. When performing pancreatic islet transplantation, by transplanting pancreatic islets and adipose tissue-derived stem cells together, it is possible to significantly improve graft survival rate of transplanted pancreatic islets, and reduce by half the number of transplanted pancreatic islets required for normalizing blood glucose level.

6 Claims, 5 Drawing Sheets

(56) References Cited

OTHER PUBLICATIONS

NPL document 'mdc_examples_nature-based_products' accessed from http://www.uspto.gov/patents/law/exam/mdc_examples_nature-based_products.pdf on Dec. 16, 2014.*

Ito, T. et al., Mesenchymal Stem Cell and Islet Co-Transplantation Promotes Graft Revascularization and Function, Transplantation, 2010, vol. 89, No. 12, pp. 1438-1445.

Sakata, N. et al., Bone Marrow Cell Co-Transplantation with Islets Improves their Vascularization and Function, Transplantation, 2010, vol. 89, No. 6, pp. 686-693.

Ohmura, Y. et al., Combined Transplantation of Pancreatic Islets and Adipose Tissue-Derived Stem Cells Enhances the Survival and Insulin Function of Islet Grafts in Diabetic Mice, Transplantation, vol. 90, No. 12, Dec. 2010, pp. 1366-1373.

Johansson, U. et al., Formation of Composite Endothelial Cell—Mesenchymal Stem Cell Islets. A Novel Approach to Promote Islet Revascularization, Diabetes, vol. 57, No. 9, Sep. 2008, pp. 2393-2401.

Supplementary European Search Report dated Apr. 17, 2014 for EP Application No. 11814752.9.

English Translation of Ito, T. et al., Mesenchymal Stem Cells (MSCs), The 44th Annual Congress of the Japan Society for Transplantation, Special Extra Issue, 2008, p. 249.

English Translation of Ito, T. et al., Mesenchymal Stem Cells (MSCs), Dai 35 Kai Sui•Suito Ishoku Kenkyukai, 2008, vol. 43, No. 3, p. 228.

English Translation of Ito, T. et al., Mesenchymal Stem Cells (MSCs), Regenerative Medicine, 2009, vol. 8 Suppl., p. 159.

English Translation of Ikemoto, T. et al., Journal of Japan Surgical Society, 2010, vol. 111, Special Extra issue (2), p. 370.

Fumimoto, Y. et al., Creation of a Rich Subcutaneous Vascular Network with Implanted Adipose Tissue-Derived Stromal Cells and Adipose Tissue Enhances Subcutaneous Grafting of Islets in Diabetic Mice, Tissue Engineering: Part C, 2009, vol. 15, No. 3, pp. 437-444.

Solari, M. et al., Marginal Mass Islet Transplantation with Autologous Mesenchymal Stem Cells Promotes Long-term Islet Allograft Survival and Sustained Normoglycemia, Journal of Autoimmunity, 2009, vol. 32, pp. 116-124.

Ito, T. et al., Mesenchymal Stem Cells (MSCs), The 44th Annual Congress of the Japan Society for Transplantation, Special Extra Issue, 2008, p. 249.

Ito, T. et al., Mesenchymal Stem Cells (MSCs), Dai 35 Kai Sui•Suito Ishoku Kenkyukai, 2008, vol. 43, No. 3, p. 228.

Ito, T. et al., Mesenchymal Stem Cells (MSCs), Regenerative Medicine, 2009, vol. 8 Suppl., p. 159.

Ikemoto, T. et al., Journal of Japan Surgical Society, 2010, vol. 111, Special Extra issue (2), p. 370.

International Search Report for PCT/JP2011/067992 dated Sep. 6, 2011.

* cited by examiner

COMBINED ISLET TRANSPLANTATION USING PANCREATIC ISLETS AND ADIPOSE TISSUE DERIVED STEM CELLS

This application is a National Stage application filed under Rule 371 based upon PCT/JP2011/067992 filed Aug. 5, 2011.

TECHNICAL FIELD

The present invention relates to a pancreatic islet transplantation graft survival improvement agent for increasing pancreatic islet graft survival rate upon pancreatic islet transplantation, and to a survival maintenance agent for maintaining survival of isolated pancreatic islets. In addition, the present invention relates to a kit for islet transplantation and a biopharmaceutical for islet transplantation using the pancreatic islet transplantation graft survival improvement agent. Furthermore, the present invention relates to a composite graft of islets and adipose tissue-derived stem cells.

BACKGROUND ART

Diabetes is a typical lifestyle-related disease, and when its symptoms worsen, risks of inducing complications such as retinopathy, nephropathy, and neuropathy increase, symptoms of apoplexy and ischemic cardiopathy develop or intensify, and the patient's QOL (Quality of Life) and life prognosis are significantly impaired. Diabetes is classified into type 1 diabetes whose onset occurs in children or youth, and type 2 diabetes whose onset occurs in adults. Type 1 diabetes is attributed to complete destruction of cells (langerhans-islet β cells of pancreas) that produce insulin, which is a blood glucose lowering hormone, and, as a result, it is known to cause erratic fluctuation of blood glucose level and various disorders. Hitherto, treatment of type 1 diabetes has depended on insulin reinforcement therapy in which insulin is administered. However, it is difficult to stably control blood glucose only through insulin administration, and, in some cases, the risk increases for acute hypoglycemic attack accompanied by a serious altered state of consciousness. Furthermore, insulin administration is merely a symptomatic therapy for type 1 diabetes, and its inability to be a fundamental cure is a problem.

As a result, in recent years, islet transplantation in which islets are removed from a pancreas of a donor for transplantation is attracting people's attention as a fundamental therapy for type 1 diabetes. Islets are injected into a portal vein of a patient through islet transplantation enter the liver, survive in portal veins all around the liver, and start secreting insulin, making it possible to fundamentally cure type 1 diabetes. Since islet transplantation is performed by drip transfusion of langerhans islets (pancreatic islets), an abdominal operation is not necessary and pancreatic juice treatment is also unnecessary; thus, when compared to whole pancreas transplantation from a brain-dead donor, which is a general organ transplantation, islet transplantation have advantages of being highly safe and having an extremely small burden on the patient.

On the other hand, islet transplantation has a problem in which transplanted islets have a poor graft survival rate and transplantation of islets obtained only from a single donor is insufficient. Therefore, with hitherto known islet transplantation, multiple donors are required for a single recipient. Furthermore, since isolated islets perish in several days outside a living body, islets isolated from a donor have to be transplanted, immediately. Furthermore, currently with hitherto known islet transplantation, insulin independent rate (proportion of recipients that do not require insulin administration) five years after transplantation in the follow-up stage becomes as low as approximately 10%. As described above, due to factors such as low graft survival rate of transplanted islets, large quantity of islets required for transplantation, and low insulin independent rate, islet transplantation has a problem of being inferior in terms of long-term outcome when compared to whole pancreas transplantation which is a highly invasive procedure for recipient.

In recent years, as a technique for increasing islets' graft survival rate in islet transplantation, a mix-transplantation, in which islets that are to be transplanted are admixed with bone marrow-derived mesenchymal stem cells (BMSC), is proposed (cf. Non-Patent Literature 1). However, this technique has drawbacks such as (1) an immunosuppressant is administered when performing the mix-transplantation, (2) a large number of BMSCs are combined, (3) the actual effect of islet transplantation cannot be evaluated since a pouch using greater omentum is formed at a site for transplantation and large quantities of islets+BMSCs are transplanted thereto, and (4) there is no reduction in the quantity of islets administered through allotransplantation.

If the quantity of to-be-transplanted islets for islet transplantation can be reduced and isolated islets can live and be cultured for an extended period of time, it becomes possible to transplant islets obtained from a single donor to multiple recipients. In such a case, it is expected that islet transplantation will rapidly spread and can greatly contribute to diabetes treatment. However, hitherto, such a technique had not been established.

CITATION LIST

Non-Patent Literature

NPL 1: Mario G. Solari et al., Journal of Autoimmunity, 32 (2009), 116-124

SUMMARY OF INVENTION

Technical Problem

An object of the present invention is to provide a pancreatic islet transplantation technique that enables to enhance graft survival rate of islets after transplantation, to culture islets isolated from living body in a living state for an extended period of time, and to reduce the number of transplanted islets required for normalizing blood glucose level.

Solution to Problem

The present inventors have conducted extensive research in order to solve the above problems, and surprisingly found that graft survival rate of transplanted pancreatic islets can be significantly improved by co-transplantation (hybrid transplantation) of islets and adipose tissue-derived stem cells (ADSCs) simultaneously when performing the islet transplantation. In addition, they have found that co-transplantation of islets and adipose tissue-derived stem cells can reduce, to about half, the number of transplanted islets required for normalizing blood glucose level. As a result of conducting further research and making further improvements based on these findings, the present inventors have confirmed that co-culturing islets and adipose tissue-derived stem cells in advance dramatically extends the lifetime of islets in vitro, and discovered that such co-culturing results in the formation of a composite (composite graft) in which adipose tissue-derived stem cells are adhered around an islet. Furthermore, the present inventors have found that islets can be engrafted at a high graft survival rate by intraportally injecting the composite so that the islets are delivered to the periphery of portal veins of the liver in a state where adipose tissue-derived stem cells and islets coexist.

The present invention has been accomplished based on the above described findings and through further research. The following describes the present invention, representatively.

Item 1. A graft survival improvement agent for pancreatic islet transplantation, comprising adipose tissue-derived stem cells.

Item 2. The graft survival improvement agent for pancreatic islet transplantation according to Item 1, wherein the adipose tissue-derived stem cells are derived from human.

Item 3. A biopharmaceutical for pancreatic islet transplantation, comprising adipose tissue-derived stem cells and pancreatic islets.

Item 4. The biopharmaceutical for pancreatic islet transplantation according to Item 3, wherein the adipose tissue-derived stem cells and pancreatic islets are derived from human.

Item 5. A kit for pancreatic islet transplantation, comprising a first cell preparation containing adipose tissue-derived stem cells and a second cell preparation containing pancreatic islets.

Item 6. The kit for pancreatic islet transplantation according to Item 5, wherein the adipose tissue-derived stem cells and the pancreatic islets are derived from human.

Item 7. A survival maintenance agent for pancreatic islets, comprising adipose tissue-derived stem cells.

Item 8. The survival maintenance agent according to Item 7, wherein the adipose tissue-derived stem cells are derived from human.

Item 9. A method for culturing pancreatic islets, the method comprising culturing pancreatic islets in the presence of adipose tissue-derived stem cells.

Item 10. The method according to Item 9, wherein the adipose tissue-derived stem cells and the pancreatic islets are derived from human.

Item 11. A composite in which adipose tissue-derived stem cells are adhered to a pancreatic islet.

Item 12. The composite according to Item 11, wherein the pancreatic islet is covered with the adipose tissue-derived stem cells.

Item 13. The composite according to Item 11 or 12, wherein the pancreatic islet and the adipose tissue-derived stem cells are derived from human.

Item 14. A pancreatic islet transplantation method, comprising simultaneous administration of pancreatic islets and adipose tissue-derived stem cells to a patient in need of a treatment of diabetes.

Item 15. A therapeutic method for diabetes, the method comprising administration of the composite according to any one of Items 11 to 13, to a patient in need of a treatment of diabetes.

Item 16. A method for producing the composite according to any one of Items 11 to 13, the method comprising co-culturing of the adipose tissue-derived stem cells and the pancreatic islets.

Item 17. A method for maintaining survival of pancreatic islets, the method comprising co-culturing of adipose tissue-derived stem cells and pancreatic islets.

Item 18. A therapeutic method for diabetes, the method comprising the steps of (A) and (B):

(A) co-culturing a pancreatic islet and adipose tissue-derived stem cells to form a composite of the pancreatic islet and the adipose tissue-derived stem cells; and (B) administering the composite to a patient in need of a treatment of diabetes.

Advantageous Effects of Invention

With the present invention, by mixing and co-transplanting adipose tissue-derived stem cells and islets, or by using a composite of adipose tissue-derived stem cells and an islet for islet transplantation, graft survival rate of islets can be improved. As a result, it is possible to reduce the amount of islets required for transplantation and the number of transplantations, and effectively treat diabetes through islet transplantation.

The present invention allows the number of islets required for transplantation to be reduced; therefore, islets obtained from a single donor can be transplanted to multiple recipients. This ameliorates shortage of donors for islets and provides an innovative technique for spreading islet transplantation into general medical care.

The present invention allows the survival of the islets to be maintained (i.e., suppress perishing of the islets) by co-culturing adipose tissue-derived stem cells with islets isolated from a living body. This makes it possible to store the islets removed from a donor in a state ready for islet transplantation for an extended period of time; therefore, the islets isolated from a single donor can be transplanted to a more suitable recipient. Furthermore, because the islets can be stably cultured in vitro while retaining their insulin secretion ability, it is possible to administer an immunosuppressant to a recipient prior to conducting islet transplantation.

DESCRIPTION OF EMBODIMENTS

I. Graft Survival Improvement Agent for Pancreatic Islet Transplantation

A graft survival improvement agent of the present invention contains adipose tissue-derived stem cells.

As described herein, adipose tissue-derived stem cells refer to pluripotent somatic stem cells existing in adipose tissues of mammals. The adipose tissue-derived stem cells of the present invention include cultured cells obtained from culturing (including successive subculturing) the somatic stem cells as long as they maintain pluripotency, ADSCs obtained through iPS (Induced Pluripotent Stem) process are also included.

An adipose tissue which is a source for adipose tissue-derived stem cells can be collected from mammals such as human, mice, rats, guinea pigs, hamsters, monkeys, cows, pigs, goats, sheep, dogs, and cats using a method known in the art such as excision and suction. From a standpoint of suppressing immunological rejection of the graft survival improvement agent of the present invention, an individual from whom an adipose tissue is collected is preferably an individual from the same species as a recipient to whom the pancreatic islet graft survival improvement agent of the present invention is applied, and is further preferably the same individual as the recipient. More specifically, when the graft survival improvement agent of the present invention is applied to human, an adipose tissue rendering adipose tissue-derived stem cells is preferably originated from human, and further preferably originated from the same human as the recipient.

Examples of the types of the adipose tissue, which is a source for adipose tissue-derived stem cells, include, but not particularly limited to, subcutaneous fat, visceral fat (including greater omentum), intramuscular fat, intermuscular fat, and the like. Among these adipose tissues, a single type of adipose tissue may be used as a source for collecting adipose tissue-derived stem cells, or two or more types of adipose tissues may be used in a combination. From a standpoint of reducing the burden on a donor when collecting an adipose tissue, the adipose tissue which becomes the source for adipose tissue-derived stem cells is preferably subcutaneous fat. Furthermore, as long as stem cells in the adipose tissue are alive, the mammal from which the adipose tissue is collected may be dead or alive.

The collection of stem cells from the adipose tissue is performed using a method known in the art. Specifically, a method of collecting stem cells from an adipose tissue through the following steps of (1) to (6) is illustrated as an example.
(1) A collected tissue is digested using an enzyme such as collagenase and trypsin after subjecting it to removal of blood constituent and slicing into small pieces if necessary.
(2) A cell population after the enzyme digestion is centrifuged at 1800 rpm for about 5 minutes, and sedimented cell population is collected.
(3) The sedimented cell population is repeatedly centrifuged for three times using the same condition as (2), and the resulting sedimented cell population is collected. With this operation, mature adipocytes are removed.
(4) The collected cell population is plated and cultured on a culture dish containing fresh medium.
(5) Non-adherent cells are removed through culture-medium replacement. At this point, adipose tissue-derived stem cells are adhered to the culture dish.
(6) Successive subculturing is conducted if necessary.

If necessary, it may be confirmed as to whether the stem cells collected from an adipose tissue have the function as pluripotent stem cells, by examining differentiation potency and cell surface markers.

In the present invention, adipose tissue-derived stem cells are used as the graft survival improvement agent for pancreatic islet transplantation. Therefore, the graft survival improvement agent for pancreatic islet transplantation can be a cell preparation that is transplanted together with islets, in order to increase graft survival rate of the transplanted islets.

Pancreatic islets, which are also referred to as langerhans islets, are cells (or lumps of cells) ordinarily having a size of 100 to 200 µm, and their main constituent cells include α-cells that secrete glucagon, β-cells that secrete insulin, δ-cells that secrete somatostatin, and PP-cells that secrete pancreatic polypeptides. The origin (donor) of the islets that are to be transplanted may be a mammal of the same species as a recipient, and, for example, when the recipient is human, human-derived islets are used.

Islets that are to be transplanted are isolated from a pancreas using a known method. The removal of a pancreas that is used as a source for isolating islets can be suitably selected depending on the type of donor. For example, when the donor is a mouse, the whole pancreas of a non-heart beating mouse may be removed to be used; and when the donor is human, the whole pancreas is removed as a graft if the donor's heart is not beating, or about 50 to 70% of the pancreas is excised for removal if the donor is alive. The graft survival improvement agent of the present invention is suitably used when transplanting islets from a non-heart beating donor, or when transplanting islets from a living donor.

In addition, specific examples of the method for isolating islets from a pancreas include a method having the following steps of (i) to (iii) when the donor is a mouse. Furthermore, when the donor is human, a method based on the Ricordi method known in the art can be illustrated as an example.
(i) An enzyme such as collagenase is allowed to uniformly penetrate and swell a pancreas. The present step is preferably performed in a low temperature condition of about 4 to 6° C. in order to prevent enzyme reaction to proceed.
(ii) The swelled pancreas is digested through enzyme reaction. The digestion through enzyme reaction is performed by exposing the swelled pancreas to a temperature that allows enzyme reaction to proceed (e.g., about 37° C.). In addition to digesting the swelled pancreas using an enzyme, the pancreas may be mechanically decomposed through vibration or the like if necessary.
(iii) Using density gradient centrifugation, islets are isolated from the cell population obtained through enzyme digestion. In the density gradient centrifugation, a part from which islets can be obtained is suitably selected depending on the rotational velocity of the centrifugal separation, the type of density gradient solution, etc.

The isolated islets may be stored in an appropriate preservation solution if necessary. The isolated islets are preferably cultured and stored together with the above described survival maintenance agent for pancreatic islets of the present invention (i.e., the adipose tissue-derived stem cells). By doing so, the isolated islets can be maintained in a living state for a further extended period of time.

The graft survival improvement agent of the present invention may include, other than the adipose tissue-derived stem cells, a carrier that is pharmaceutically acceptable and that does not adversely affect the adipose tissue-derived stem cells. Specific examples of such carrier include saline solution, PBS, culture media, protein pharmaceuticals including albumin, pancreatic islet preservation solutions, etc.

The administration dose of the graft survival improvement agent of the present invention is selected as appropriate in accordance with the transplantation route, presence of a composite formed with an islet, the quantity of islets that are to be transplanted, the severity of the symptom of a recipient, etc. For example, when the graft survival improvement agent in a state of not forming a composite with an islet is mixed together with islets and injected to a recipient having a body weight of 50 kg at a location under the renal capsule, in greater omentum, or in subcutaneous tissue; the administration dose for a single islet transplantation is, for example, $5.0 \times 10^7$ to $1.0 \times 10^9$ cells, and is preferably $1.0 \times 10^8$ to $5.0 \times 10^8$ cells. When the graft survival improvement agent of the present invention is intraportally administered in a form of a composite of an islet and adipose tissue-derived stem cells to a recipient having a body weight of 50 kg; the administration dose for a single islet transplantation is, for example, $1.0 \times 10^8$ to $2.0 \times 10^9$ cells, and is preferably $5.0 \times 10^8$ to $1.0 \times 10^9$ cells. Therefore, the graft survival improvement agent of the present invention can include the number of adipose tissue-derived stem cells that allows the quantity of islets for a single transplantation to be within the above described range.

The administration dose for the graft survival improvement agent of the present invention and the ratio of to-be-transplanted islets are also suitably selected in accordance with the transplantation route, the quantity of islets to be transplanted, the severity of the symptom of a recipient, etc. For example, when the adipose tissue-derived stem cells, which is the graft survival improvement agent, in a state of not forming a later described composite with islets is mixed together with islets and injected at a location under the renal capsule, in greater omentum, or in subcutaneous tissue; with regard to the ratio of the number of transplanted islets with respect to the number of adipose tissue-derived stem cells included in the graft survival improvement agent, adipose tissue-derived stem cells:islets is, for example, 400:1 to 3000:1 or 500:1 to 2000:1, or is preferably 600:1 to 1500:1. Furthermore, when the adipose tissue-derived stem cells, which is the graft survival improvement agent, in a state of being a composite with an islet is injected into a portal vein; with regard to the ratio of the number of transplanted islets with respect to the number of adipose tissue-derived stem cells included in the graft survival improvement agent, adipose tissue-derived stem cells: islets is, for example, 500:1 to 3500:1 or 1000:1 to 3000:1, or is preferably 1500:1 to 2500:1. Based on this, the ratio based on cell number can be obtained, since an islet normally consists of approximately 1000 to 2000 islets.

The quantity of islets transplanted together with the graft survival improvement agent of the present invention is selected as appropriate in accordance with the severity of the symptom of a recipient, etc. Generally, the number of transplanted islets for a single islet transplantation for a recipient having a body weight of 50 kg is normally sufficient when the number is within a range of $5.0 \times 10^4$ to $1.0 \times 10^7$. However, since the graft survival rate for islets can be increased when the graft survival improvement agent of the present invention is used, it is possible to obtain sufficient insulin independence even when the number of transplanted islets for a single islet transplantation is reduced to $1 \times 10^5$ to $2 \times 10^6$, preferably to $5 \times 10^5$ to $1.5 \times 10^6$, and further preferably to $1 \times 10^6$ to $1.5 \times 10^6$ with respect to a 50 kg adult patient. With such number of transplanted islets, it becomes possible to transplant islets obtained from a single donor to multiple recipients.

As long as the graft survival improvement agent of the present invention is administered together with islets that are to be transplanted, there is no particular limitation in the administration mode; and the graft survival improvement agent may be administered in a state of being mixed with islets, or the graft survival improvement agent may be administered alone before or after islets are administered. From a standpoint of further improving graft survival of islets, preferably, the graft survival improvement agent is administered in a state of being mixed with islets, i.e., transplanting a cell preparation obtained by mixing adipose tissue-derived stem cells and islets, and, more preferably, the graft survival improvement agent is administered as the later described composite in which an islet and adipose tissue-derived stem cells are adhered to each other.

As long as the graft survival improvement agent of the present invention is capable of enhancing/improving graft survival of islets, there is no particular limitation in its administration route, and the administration route may be direct injection (transplantation) in blood in a portal vein or the like, or transplantation in nonvascular tissues such as in subcutaneous tissue, in greater omentum, under the renal capsule, or the like. When the graft survival improvement agent of the present invention is administered as the later described composite of an islet and adipose tissue-derived stem cells, injection in blood in a portal vein or the like is preferable; and when the graft survival improvement agent is administered separately from islets, simultaneous injection of a mixture of islets and adipose tissue-derived stem cells at a location under the renal capsule, in greater omentum or in subcutaneous tissue is preferable.

Although the graft survival improvement agent of the present invention is administered to patients (recipients) whose insulin function of islet graft is reduced or lost, e.g., patients of type 1 diabetes or the like who require islet transplantation; the graft survival improvement agent has expectation of being applied to patients of type 2 diabetes (brittle type) etc., and further, the graft survival improvement agent is expected to be effective when applied to diabetics overall. Preferable patients are type 1 diabetics who require islet transplantation.

II. Biopharmaceutical for Pancreatic Islet Transplantation

A biopharmaceutical for pancreatic islet transplantation of the present invention includes the above described graft survival improvement agent and islets that are to be transplanted.

The biopharmaceutical for pancreatic islet transplantation of the present invention has the above described adipose tissue-derived stem cells and islets to be transplanted mixed therein, and may be a biopharmaceutical enabling co-transplantation of these cells as a mixture. Furthermore, the biopharmaceutical for pancreatic islet transplantation of the present invention may be a biopharmaceutical for pancreatic islet transplantation including the later described composite (hereinafter, may be referred to as "composite graft") in which adipose tissue-derived stem cells are adhered to an islet.

The biopharmaceutical for pancreatic islet transplantation of the present invention may include, other than the adipose tissue-derived stem cells and islets to be transplanted or the above described composite, a carrier that is pharmaceutically acceptable and that does not adversely affect these cells. Specific examples of such carrier include saline solution, PBS, culture media, protein pharmaceuticals such as albumin, pancreatic islet preservation solutions, etc.

With regard to the biopharmaceutical for pancreatic islet transplantation of the present invention, the description in "I. Graft Survival Improvement Agent for Pancreatic Islet Transplantation" also applies for the administration quantity (transplantation quantity) of the adipose tissue-derived stem cells and islets, the ratio of these cells, the administration method of the biopharmaceutical, patients to whom the biopharmaceutical is administered, etc.

III. Kit for Pancreatic Islet Transplantation

A kit for pancreatic islet transplantation of the present invention includes a first cell preparation containing the above described graft survival improvement agent and a second cell preparation containing islets that are to be transplanted.

The first cell preparation is a cell preparation containing adipose tissue-derived stem cells, and may also contain, other than the adipose tissue-derived stem cells, a carrier that is pharmaceutically acceptable and that does not adversely affect the adipose tissue-derived stem cells. Specific examples of such carrier include saline solution, protein pharmaceuticals such as albumin, PBS, culture media, etc.

The second cell preparation is a cell preparation containing islets that are to be transplanted, and may include, other than the islets, a carrier that is pharmaceutically acceptable and that does not adversely affect the islets. Specific examples of such carrier include saline solution, PBS, culture media, protein pharmaceuticals such as albumin, pancreatic islet preservation solutions, etc.

The kit for pancreatic islet transplantation of the present invention comprises the first cell preparation and the second cell preparation separately, and the first cell preparation and the second cell preparation may be each administered individually, or the first cell preparation and the second cell preparation may be mixed in advance and then administered. When the first cell preparation and the second cell preparation are administered individually, the second cell preparation may be administered after administration of the first cell preparation, or the first cell preparation may be administered after administration of the second cell preparation.

With regard to the first cell preparation, the description in "I. Graft Survival Improvement Agent for Pancreatic Islet Transplantation" also applies for the administration quantity (transplantation quantity) of the adipose tissue-derived stem cells, administration method of the first cell preparation, etc. The kit can also be used as a kit for producing the later described composite in which adipose tissue-derived stem cells are adhered to islets.

Furthermore, the description in "I. Graft Survival Improvement Agent for Pancreatic Islet Transplantation" also applies for the ratio of the adipose tissue-derived stem cells included in the first cell preparation and the islets included in the second cell preparation. Further, the description in "I. Graft Survival Improvement Agent for Pancreatic Islet Transplantation" also applies for patients to whom the kit for pancreatic islet transplantation of the present invention is applied.

IV. Survival Maintenance Agent for Pancreatic Islets

A survival maintenance agent for pancreatic islets of the present invention includes adipose tissue-derived stem cells. The adipose tissue-derived stem cells included in the survival maintenance agent for pancreatic islets are identical to the adipose tissue-derived stem cells described in "I. Graft Survival Improvement Agent for Pancreatic Islet Transplantation." There is no particular limitation in the islets whose survival is maintained by the survival maintenance agent of the present invention, and the islets are identical to the islets described in "I. Graft Survival Improvement Agent for Pancreatic Islet Transplantation."

When islets isolated from a living body are cultured using the survival maintenance agent for pancreatic islets of the present invention, survival of the islets can be maintained (i.e., perishing of the islets can be suppressed) compared to a case where the survival maintenance agent is not used. For example, islets derived from mice ordinarily perish through apoptosis after being isolated from a living body and cultured for 2 to 3 days. However, by using the survival maintenance agent for pancreatic islets of the present invention, survival of islets can be maintained for 6 days or more after being isolated from a living body. Here, survival of islets refers to islets being in a living state suitable for islet transplantation. Whether or not islets are alive in a state suitable for islet transplantation can be determined by, for example, their shapes observed through microscopy and by their ability to produce insulin after being stimulated with glucose (i.e., static incubation).

There is no particular limitation in the culturing of islets using the survival maintenance agent for pancreatic islets of the present invention, as long as survival of the islets is maintained; and, ordinarily, co-culturing adipose tissue-derived stem cells, which are the survival maintenance agent, and islets, is performed under a condition suitable for culturing islets. There is no particular limitation in the culturing condition as long as it is suitable for culturing islets; and, for example, the culturing can be performed in the presence of 15 to 25% $O_2$ and 3 to 6% $CO_2$ at a temperature around 37° C. using a commercially available culture medium (e.g., DMEM).

For the culturing, a commercially available microwell plate commonly used for culturing islets may be appropriately selected; and a plate whose surface is treated so that cells rarely adhere to a container is preferably used. Examples of such plate include a plate (e.g., Corning Ultra-low attachment multiwell plates from Sigma Aldrich Corp.) whose surface is coated with EDTA, heparin, and the like. When a container or plate suppressing adherence of cells to the surface of the container is used, the adipose tissue-derived stem cells and the islets can freely move within a culture. This promotes adherence of the adipose tissue-derived stem cells onto the islets.

When islets are cultured using the survival maintenance agent for pancreatic islets of the present invention, there is no particular limitation in the existence ratio of the survival maintenance agent (i.e., the adipose tissue-derived stem cells) and the islets; and, for example, adipose tissue-derived stem cells:islets is ordinarily 500:1 to 3500:1, or 1000:1 to 3000:1, or is preferably 1500:1 to 2500:1. Furthermore, there is no particular limitation in the number of islets existing in 1 ml of culture medium, and the number per 1 ml can be, for example, 5 to 30, preferably 10 to 25, and more preferably 12 to 20.

The survival maintenance agent for pancreatic islets of the present invention may include, other than the adipose tissue-derived stem cells, a carrier that is pharmaceutically acceptable and that does not adversely affect the adipose tissue-derived stem cells. Specific examples of such carrier include saline solution, PBS, culture media, protein pharmaceuticals containing albumin, pancreatic islet preservation solutions, etc.

V. Composite in which Adipose Tissue-Derived Stem Cells are Adhered to a Pancreatic Islet The present invention relates to a composite (composite graft) in which adipose tissue-derived stem cells are adhered to an islet. It should be noted that the islet and adipose tissue-derived stem cells forming the composite are identical to those described in "I. Graft Survival Improvement Agent for Pancreatic Islet Transplantation."

As long as adipose tissue-derived stem cells are directly adhered to an islet, there is no particular limitation in the structure of the composite; and, preferably, the composite has a structure in which at least one part of an islet is covered with adipose tissue-derived stem cells. More preferably, when observed through microscopy, not less than 30%, preferably not less than 40%, more preferably not less than 50%, further preferably not less than 60%, more further preferably not less than 70%, even further preferably not less than 80%, and even more further preferably not less than 90% of the surface of an islet is covered with adipose tissue-derived stem cells. Particularly preferably, the whole surface of an islet is covered with adipose tissue-derived stem cells. By having a larger part of an islet covered with adipose tissue-derived stem cells, it is thought that the graft survival improving effect and the survival maintaining effect by the adipose tissue-derived stem cells are synergistically exerted.

Figure 4:
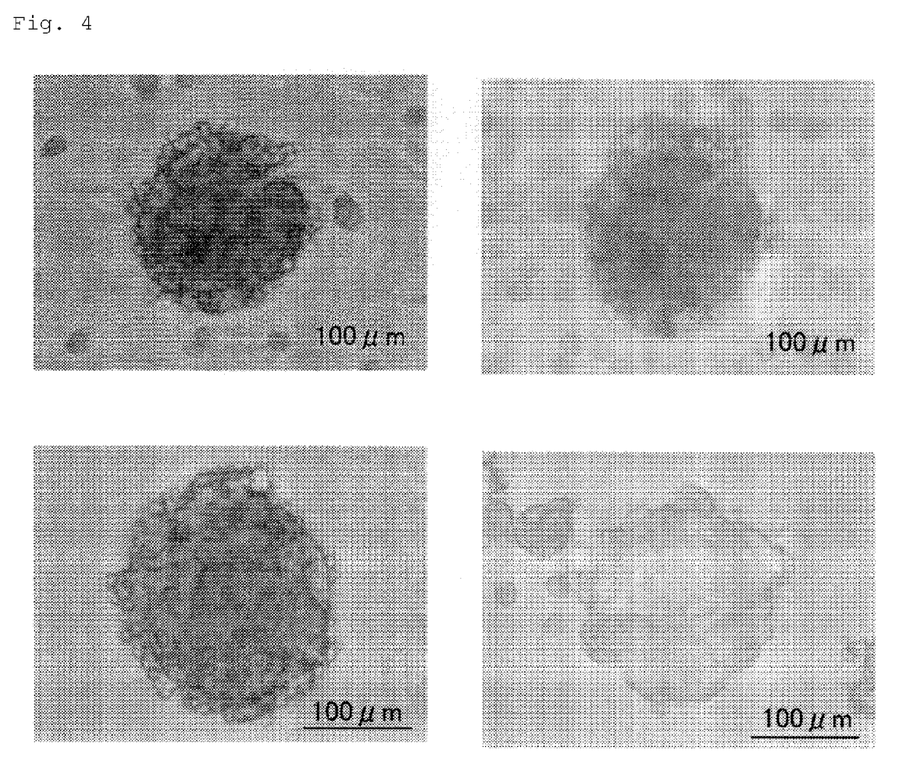
FIG. 4 shows the states before and after the co-culturing of islets and adipose tissue-derived stem cells. The upper left picture shows the state before culturing islets alone. The lower left picture shows the islets cultured in the absence of adipose tissue-derived stem cells. The upper right picture shows the state after islets and adipose tissue-derived stem cells were added to a medium but before they were cultured. The lower right picture shows the state after the islets and adipose tissue-derived stem cells were co-cultured.

As shown in FIG. 4, an islet is normally spherical, and the expression "having the whole surface of an islet covered with adipose tissue-derived stem cells" means a spherical islet is wrapped with a layer of adipose tissue-derived stem cells as shown in the lower right picture in FIG. 4. It should be noted that, in a color version of the lower right picture in FIG. 4, it is obvious that adipose tissue-derived stem cells that glow in green due to GFP (Green Fluorescent Protein) completely cover an islet.

There is no particular limitation in the ratio of the numbers of adipose tissue-derived stem cells and islets forming a single composite, but ordinarily, the composite has a structure in which a single islet is covered with a large number of adipose tissue-derived stem cells as shown in the lower right picture in FIG. 4. There is no particular limitation in the number of adipose tissue-derived stem cells adhering onto a single islet, and, for example, the number is ordinarily not less than 10, preferably not less than 20, more preferably not less than 30, further preferably not less than 40, and more further preferably not less than 50. Furthermore, there is no particular limitation in the number of adipose tissue-derived stem cells adhering onto a single islet, and, assuming the number required for total coverage, the number is ordinarily, for example, not more than 5000, preferably not more than 4500, more preferably not more than 3000, and further preferably not more than 2500.

By having an islet and adipose tissue-derived stem cells exist in close contact, the composite of the present invention can more effectively exert the pancreatic islet survival maintaining effect and graft survival improving effect for islet transplantation by the adipose tissue-derived stem cells. More specifically, in order to improve the graft survival rate of islet transplantation using adipose tissue-derived stem cells, it is preferably to have adipose tissue-derived stem cells exist at the location where an islet is grafted to survive, and to have the islet be alive. Since adipose tissue-derived stem cells are adhered onto an islet in the composite, adipose tissue-derived stem cells will inevitably exist at the location where the islet forming the composite is grafted to survive. This promotes graft survival of the islet and prevents perishing of the islet.

As long as the graft survival enhancing action for the pancreatic islet and the pancreatic islet survival maintenance action attributable to the presence of adipose tissue-derived stem cells are not adversely affected, other cells, proteins, sugars, etc., may be additionally adhered to the composite of the present invention.

There is no particular limitation in the method for producing the composite in which adipose tissue-derived stem cells are adhered to islets, and, for example, the composite can be obtained by co-culturing islets and adipose tissue-derived stem cells. The co-culturing of islets and adipose tissue-derived stem cells may be performed under the condition described in "IV. Survival Maintenance Agent for Pancreatic Islets." There is no particular limitation in the culturing time as long as the composite is formed, and the time is ordinarily 10 to 48 hours, preferably 18 to 48 hours, and more preferably 24 to 36 hours.

There is no particular limitation in the ratio of the numbers of adipose tissue-derived stem cells and islets added to a culture medium to form the composite, and, ordinarily, pancreatic islets:adipose tissue-derived stem cells is 1:10 to 5000, preferably 1:100 to 4500, more preferably 1:300 to 4000, further preferably 1:500 to 3500, and even further preferably 1:800 to 3000.

VI. Therapeutic Method for Diabetes and Pancreatic Islet Transplantation Method

The present invention relates to a method for treating diabetes by simultaneously administering islets and adipose tissue-derived stem cells and transplanting islets to a patient requiring a treatment for diabetes. There is no particular limitation in the patient as long as the patient requires a treatment for diabetes, and examples of such patient include type 1 diabetics, type 2 diabetics, and the like. Preferably, the patient is a type 1 diabetic requiring islet transplantation for treating diabetes.

Simultaneous administration of islets and adipose tissue-derived cells means administration of both of them in a single islet transplantation operation. Therefore, simultaneous administration includes not only administration of a mixture of islets and adipose tissue-derived stem cells, but also includes administration of either islets or adipose tissue-derived stem cells in advance, and then administration of the other. Furthermore, simultaneous administration also includes administration of the composite. Administration of the composite is preferable.

As long as graft survival of islets can be enhanced/improved, there is no particular limitation in the administration route of the islets and adipose tissue-derived stem cells, and, for example, the administration route may be injection in blood in a portal vein or the like, or direct injection to nonvascular tissues such as in subcutaneous tissue, in greater omentum, under the renal capsule, or the like. When the graft survival improvement agent of the present invention is administered as the later described composite of an islet and adipose tissue-derived stem cells, injecting the graft survival improvement agent in blood in a portal vein or the like is preferable; and when the graft survival improvement agent is administered separately from islets, injection at a location under the renal capsule, in greater omentum, or in subcutaneous tissue is preferable.

When administering islets and adipose tissue-derived cells successively or in a mixed state, the administration dose for a single islet transplantation is as described in the above parts of I to III. There is no particular limitation in the administration dose when administering the composite state as long as the therapeutic effect is obtained. For example, the number of the composites administered for a single islet transplantation may be, ordinarily, within a range of $5.0 \times 10^4$ to $1.0 \times 10^6$ when administration is performed to a portal vein of a recipient having a body weight of 50 kg. However, since the graft survival rate for islets can be increased when the graft survival improvement agent of the present invention is used, it is possible to obtain sufficient insulin independence even when the number of transplanted composites for a single islet transplantation is reduced to 1×10$^5$ to 2×10$^6$, preferably to 5×10$^5$ to 1.5×10$^6$, and further preferably to 1×10$^6$ to 1.5×10$^6$ with respect to a 50 kg adult patient. With such number of transplanted islets, it becomes possible to transplant islets obtained from a single donor to multiple recipients.

EXAMPLES

The present invention is described in further detail with reference to Examples. However, the scope of the invention is not limited to these Examples.

Example 1

Hybrid Transplantation of Adipose Tissue-Derived Stem Cells and Pancreatic Islets 1. Collection of Adipose Tissue-Derived Stem Cells
Adipose tissue-derived stem cells were extracted from mice following the procedure described below.
(1) C57BL/6J mice (CLEA Japan, Inc.) were anesthetized, an antiseptic solution was applied thereto, and the mice were shaved with a razor.
(2) Adipose tissue (subcutaneous adipose tissue and visceral adipose tissue) was extracted from the mice, weighed, and placed in a 50-mL tube holding 20 mL of PBS (phosphate buffered saline) that contained an antibiotic (Antibiotic Antimycotic Solution (100×); Sigma; A5955-100ML)
(3) The adipose tissue was washed by mixing in a 50-mL tube. The washing process was repeated three times while exchanging the PBS containing the antibiotic.
(4) The washed adipose tissue was added to 10 mL of a culture medium (DMEM, high glucose) containing 10 mg of collagenase (type II) (Collagenase; Sigma; C 6885-500MG) and 100 μL of antibiotic (Antibiotic Antimycotic Solution (100×); Sigma; A5955-100ML). The adipose tissue was minced with scissors and incubated at 37° C. for 30 minutes while applying mechanical decomposition through vibration or the like.
(5) The adipose tissue, treated with collagenase was minced with scissors again and incubated at 37° C. for 30 minutes while applying mechanical decomposition through vibration or the like.
(6) A solution containing the adipose tissue treated with collagenase was filtered with a 1-mm strainer, and the filtrate was collected.
(7) The filtrate was centrifuged at 1800 rpm for 5 minutes, and the supernatant was removed.
(8) 10 mL of a culture medium (DMEM, high glucose) containing 10% by volume of FBS (fetal bovine serum), 1% by volume of antibiotic (Antibiotic Antimycotic Solution (100×); Sigma; A5955-100ML) and 0.2 mM of L-ascorbic acid (hereunder this culture medium is simply referred to as a culture medium) was added to the sedimented cell population, followed by gentle stirring. The result was filtered with a 70-μm cell strainer and then the filtrate was collected. Thereafter, the collected filtrate was centrifuged at 1800 rpm for 5 minutes, and the supernatant was removed. This operation was repeated three times. Because mature adipose cells were floating in the culture medium, they were removed by this operation.
(9) The collected cell population was placed in a culture medium in a 10-cm dish and cultured under the conditions of 37° C., 20% $O_2$, and 5% $CO_2$.
(10) The next day, the culture supernatant was removed, fresh culture medium was added, and the culturing was continued.

The adipose tissue-derived stem cells became subconfluent 2 to 4 days after the initiation of culturing.
2. Isolation of Pancreatic Islets
The islets were isolated from mice according to the following procedure.
(1) A 1-mg/mL collagenase type VIII/ET-Kyoto solution (swelling solution) was prepared in an amount of 5 mL per BALB/cA donor mouse (CLEA Japan, Inc.). In order to prevent deactivation, the swelling solution was preserved on ice.
(2) The donor mice were anesthetized by injecting 2.5% tribromoethanol (product name: Avertin, 8 μL/g body weight) into the abdominal cavity.
(3) The donor mice were subjected to laparotomy and then the common bile duct was isolated. A 30-G needle with syringe containing swelling solution was inserted into the common bile duct from the hepatic portal region toward the duodenum to perform cannulation, and 3 to 5 mL of the swelling solution was injected. Here, the hilum of the spleen was fully swollen.
(4) The swollen pancreas was recovered and placed into a 50-mL conical tube and then ice-cooled. Each conical tube contained the swollen pancreas of 1 to 2 donor mice.
(5) In a hot bath preheated to 37° C., the 50-mL conical tubes containing the swollen pancreases were placed and gently shuffled for 15 minutes to digest them.
(6) After digestion for 15 minutes, 30 mL of cooled ET-Kyoto solution was added thereto, and slowly pipetted using a 25-mL pipette to loosen the digested swollen pancreases. Thereafter, the cooled ET-Kyoto solution was added thereto to completely fill the 50-mL conical tube and then the digestive reaction was stopped.
(7) Centrifugation was performed at 1200 rpm and 4° C. for 2 minutes. Subsequently, after removing the supernatant, 30 mL of cooled ET-Kyoto solution was added thereto and slowly pipetted using a 25 mL pipette to fully loosen the tissues.
(8) The solution containing the loosened tissues was filtered using a 1-mm cell strainer, and then the filtrate was collected.
(9) The filtrate was centrifuged at 1200 rpm and 4° C. for 2 minutes. The supernatant was removed, and 10 mL of cooled ET-Kyoto solution was added to the portion for each donor mouse. After slowly pipetting using a 25-mL pipette, the portion for each mouse was transferred to a tube (FALCON round bottom tube).
(10) Centrifugation was performed at 1200 rpm and 4° C. for 2 minutes. After the supernatant was removed, 2 mL of 25% by volume of OptiPrep (iodixanol)/ET-Kyoto solution was added thereto, followed by stirring. Thereafter, 2 mL of 25% by volume OptiPrep (iodixanol)/ET-Kyoto solution was further added to the tube, and the mixture was stirred.
(11) 2 mL each of 22.5% by volume, 20% by volume, and 11.1% by volume OptiPrep/ET-Kyoto solution was added extremely slowly while turning the tube to form layers inside the tube.
(12) Centrifugation was performed at 2500 rpm and 4° C. for 15 minutes.
(13) By the operation of step (12), islets localized in the layer between the 20% by volume OptiPrep/ET-Kyoto solution and the 11.1% by volume OptiPrep/ET-Kyoto solution were collected and placed into a 15-mL tube.
(14) Centrifugation was performed at 800 rpm and 4° C. for 5 minutes, and the islets were transferred to a dish containing RPMI complete culture medium.
3. Transplantation of Pancreatic Islets to Mouse
(1) The isolated islets were placed in a 3.5 cm diameter dish, and stained with dithizone. Thereafter, the number of islets having a diameter of 100 μm or larger was counted.

(2) A polyethylene tube (PE50, Clay Adams™) was connected to a 50-μL Hamilton syringe, and 200 islets were collected in the polyethylene tube.
(3) The polyethylene tube was folded in half and placed in a 15-mL centrifuge tube in such a manner that the stump faced up. Subsequently, centrifugation was performed at 1500 rpm and 4° C. for 5 minutes, and islets were collected in one place in the polyethylene tube.
(4) Using a 2-mM EDTA/PBS solution, the adipose tissue-derived stem cells were collected from the dish and the number of cells was counted.
(5) $2 \times 10^5$ of adipose tissue-derived stem cells were suspended in 50 μL of PBS.
(6) A polyethylene tube (PE50, Clay Adams™) was connected to a 50-μL Hamilton syringe, and $2 \times 10^5$ of adipose tissue-derived stem cells were placed in a polyethylene tube together with 50 μL of PBS.
(7) Centrifugation was performed at 1500 rpm and 4° C. for 5 minutes, and the adipose tissue-derived stem cells were collected in one place in the polyethylene tube.
(8) C57BL/6J mice (CLEA Japan, Inc.), which are a type I diabetic model mouse, were anesthetized by injecting 2.5% tribromoethanol (8 μL/g body weight) into the abdominal cavity.
(9) The mice were subjected to a skin incision in the right side of the abdomen, the right kidney and right hepatic lobe were identified over the peritoneum, and the peritoneum was opened immediately above the right kidney to expose the right kidney.
(10) A small incision was made in the right renal capsule, and a polyethylene tube containing adipose tissue-derived stem cells was inserted under the capsule. After injecting the adipose tissue-derived stem cells, the tube was extracted.
(11) Subsequently, the polyethylene tube containing islets was inserted under the capsule from the same insertion point. After injecting the islets, the tube was extracted. Step (11) and Step (10) may be conducted in reverse order, so that the adipose tissue-derived stem cells are injected after injecting the islets.
(12) After repositioning the right kidney in the abdominal cavity, the peritoneum and skin were closed into a single layer using a 5-0 PDS suture, completing the transplantation.
(13) After the completion of the transplantation, the mice were kept under normal breeding conditions.

Comparative Example 1

Transplantation of Pancreatic Islets Alone

Pancreatic islets (200 islets) were transplanted to C57BL/6J mice in the same manner as in Example 1 described above except that the adipose tissue-derived stem cells were not transplanted.

Example 2

Evaluation of Survival Rate of Pancreatic Islets Transplanted to Mouse

Figure 1:
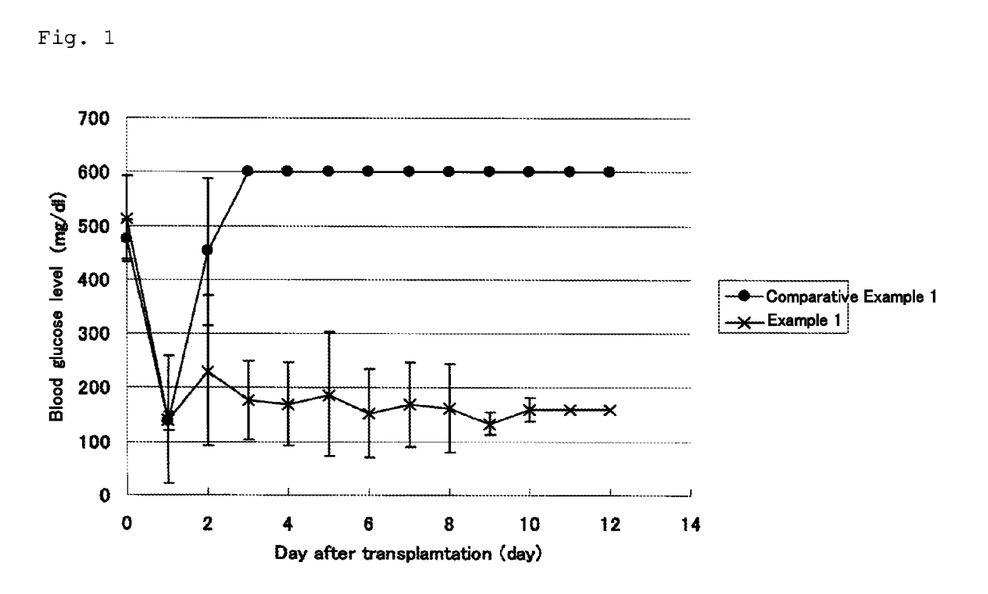
FIG. 1 shows a result of the temporal measurement of blood glucose levels in mice transplanted simultaneously with adipose tissue-derived stem cells and islets (Example 1), and in mice transplanted only with pancreatic islets (Comparative Example 1).
Figure 2:
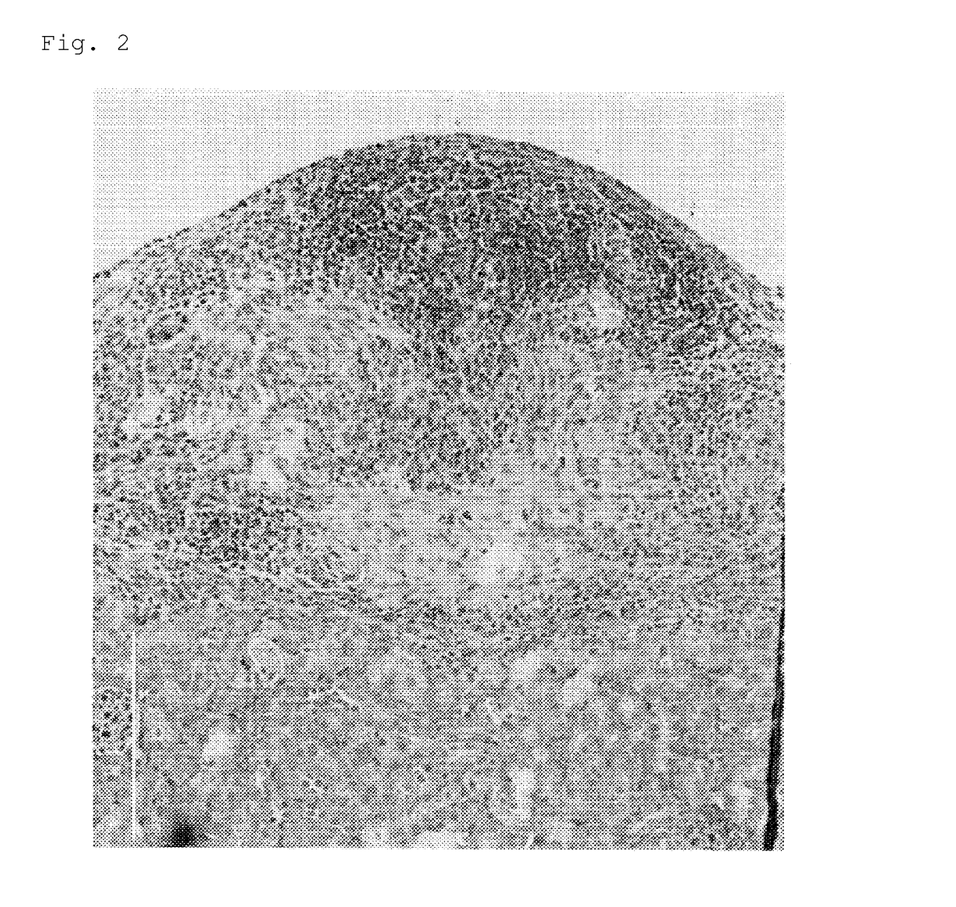
FIG. 2 shows a result of an observation of an islet tissue that originates from mice transplanted simultaneously with adipose tissue-derived stem cells and islets (Example 1). The islet tissue was removed and stained using HE stain 10 days after the islet transplantation. In the figure, the length of the bar is 200 μm.

The blood glucose levels of the C57BL/6J mice that had been subjected to islet transplantation in Examples 1 and Comparative Example 1 were measured with time for 11 days.
The results are shown in FIG. 1. The C57BL/6J mice to which pancreatic islets (200 islets) were transplanted alone showed an increase in blood glucose level from the 3rd day after the transplantation and onward. These findings revealed that the transplanted islets were not grafted. In contrast, in the C57BL/6J mice to which adipose tissue-derived stem cells ($2 \times 10^5$ cells) were transplanted simultaneously with pancreatic islets (200 islets), the blood glucose was lowered to a normal level and maintained even 11 days after the transplantation. This confirmed that the transplanted islets were sufficiently engrafted.
Considering the fact that the number of pancreatic islets (200 islets) employed in this experiment is equivalent to half of the number of islets that should usually be employed in islet transplantation to a type I diabetic mouse (400 islets), the results of this experiment confirmed that the transplanted islets can be engrafted and hyperglycemia can be ameliorated by the hybrid transplantation of adipose tissue-derived stem cells and islets even when the number of islets transplanted is reduced to half. This is presumably because a large number of transplanted islets were able to be engrafted due to the vascularization from the adipose tissue-derived stem cells, and the hyperglycemia was ameliorated due to the regeneration of islet tissues from the adipose tissue-derived stem cells.
On day 11, islet tissue was extracted from the C57BL/6J mice to which adipose tissue-derived stem cells and islets were simultaneously transplanted. The islet tissue was stained using HE stain and then observed. FIG. 2 shows the results. As is clear from FIG. 2, in the C57BL/6J mice to which adipose tissue-derived stem cells and islets were transplanted at the same time, it was confirmed that transplanted islets were engrafted and that attacks to the transplanted pancreatic islets by permeating inflammatory cells, such as lymphocytes associated with rejection, were blocked.

Example 3

Evaluation of Glucose Tolerance of Pancreatic Islets Transplanted Mice

Figure 3:
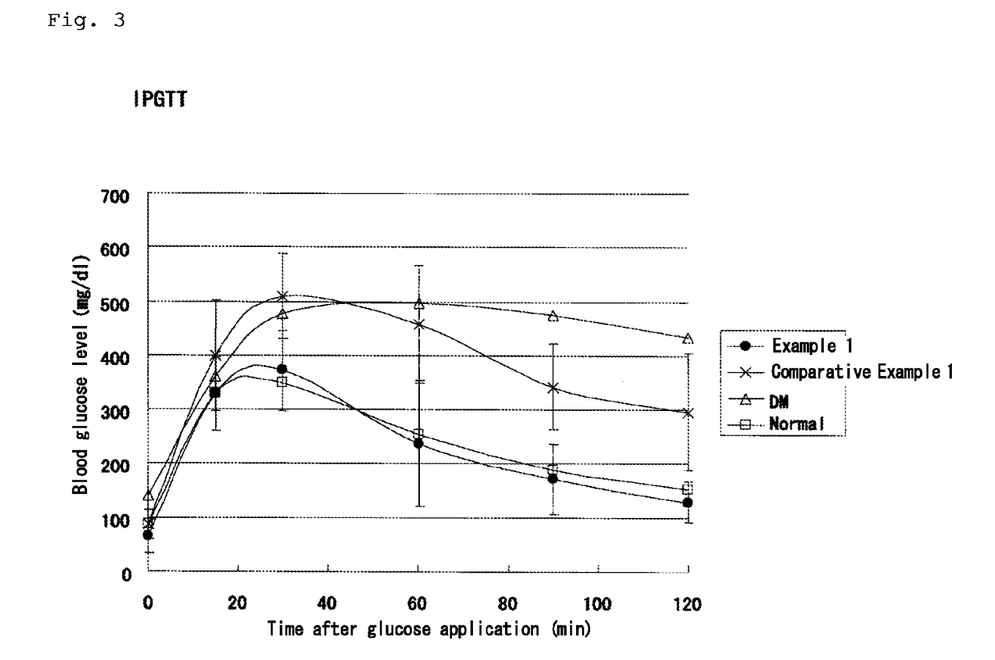
FIG. 3 is a result of intraperitoneal glucose tolerance tests (IPGTT) performed 10 days after islet transplantation to mice transplanted simultaneously with adipose tissue-derived stem cells and islets (Example 1), and to mice transplanted only with islets (Comparative Example 1).

On day 10, a 0.4-M glucose solution was injected into the abdominal cavity of the C57BL/6J mice that had been subjected to islet transplantation in Example 1 and Comparative Example 1 in an amount of 2 g/kg body weight to perform an intraperitoneal glucose tolerance test (IPGTT). The blood glucose levels were measured with time until 120 minutes had passed from the injection. As controls, the IPGTT was performed under the same conditions as described above, using C57BL/6J mice that were made diabetic (DM, hereunder referred to as diabetic model mouse) and using normal BALB/cA mice (Normal), and the blood glucose levels thereof were measured with time.
FIG. 3 shows the results. In the C57BL/6J mice to which only pancreatic islets (200 islets) were transplanted, a high blood glucose level was observed even 120 minutes after the application of the glucose load, the glucose tolerance was not normalized, and the same diabetic pattern of change in blood glucose level as that of diabetic model Trice was observed. In contrast, in C57BL/6J mice to which adipose tissue-derived stem cells ($2 \times 10^5$ cells) and pancreatic islets (200 islets) were simultaneously transplanted, the blood glucose level was lowered to a normal level 120 minutes after the application of the glucose load. More specifically, the mice exhibited the same pattern of change in blood glucose level as normal mice (non-diabetic mouse), revealing that the glucose tolerance was normalized.

Example 4

Production of Composite Graft of Pancreatic Islet and Adipose Tissue-Derived Stem Cells (1) Pancreatic islets were collected from 10- to 15-week-old C57BL/6J mice (male: CLEA Japan, Inc.) according to the procedure of Example 1 described above.

(2) Adipose tissue-derived stem cells were collected from 10- to 15-week-old eGFP-C57BL/6J mice (male: CLEA Japan, Inc.) according to the procedure of Example 1 described above.

(3) A DMEM (Sigma, D6046: normal glucose) containing 10% by volume FBS and 1% by volume antibiotic (Antibiotic Antimycotic Solution (100×); Sigma; A5955-100ML) was added to an Ultra-Low attachment multiwell plate (Sigma, Corning™, CLS3471) in an amount of 3 mL/well. To the Ultra-Low attachment multiwell plate, the islets and the adipose tissue-derived stem cells collected in steps (1) and (2) were seeded in such a manner that each well contained 50 islets and 10000 adipose tissue-derived stem cells. There is no particular order in which the islets and adipose tissue-derived stem cells are seeded. An islet is a cell population comprising about 1000 to 2000 cells (including α, β, and δ cells). Note that the term "normal glucose" indicates that glucose is contained in a concentration of 100 mg/dL.

(4) The plate to which the islets and the adipose tissue-derived stem cells were seeded in Step (3) above was subjected to static culturing for 24 hours under the conditions of 20% $O_2$ and 5% $CO_2$, at 37° C.

(5) For comparison, only islets were seeded in Step (3) above and cultured under the same conditions as in Step (4).

(6) The state of the cells in each well was observed using a microscope (product name: All-in-One, produced by Keyence Corporation) before and after culturing. FIG. 4 shows representative pictures of the morphological findings before and after culturing.

In FIG. 4, the upper left picture shows the state before culturing the islets alone. The lower left picture shows the state after culturing islets alone. The upper right picture shows the state before culturing islets and adipose tissue-derived stem cells. The lower right picture shows the state after co-culturing islets and adipose tissue-derived stem cells. These pictures reveal that when islets are cultured alone, there is no particular change in the form of the cell; however, when islets and adipose tissue-derived stem cells are co-cultured, the adipose tissue-derived stem cells adhere around the islets, so that a composite (i.e., composite graft) comprising an islet covered with adipose tissue-derived stem cells is formed.

Example 5

Figure 5:
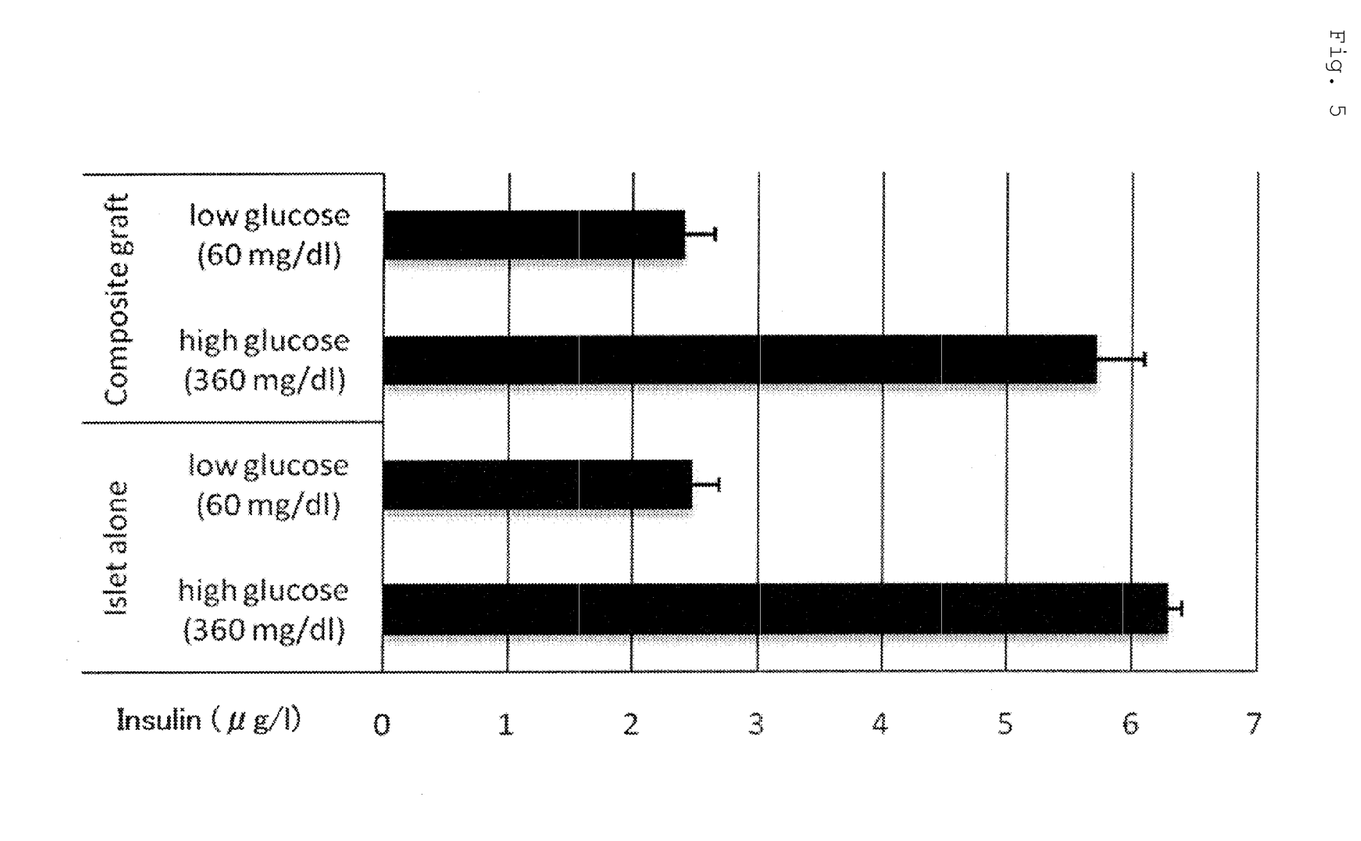
FIG. 5 shows glucose reactivity of islets cultured alone and composites having adipose tissue-derived stem cells adhered onto an islet.

Glucose Responsibility of Composite of Pancreatic Islet and Adipose Tissue-Derived Stem Cells Islets alone or islets covered with adipose tissue-derived stem cells (composite graft) after culturing for 24 hours obtained in Example 4 were subjected to static culturing for one hour in a low-glucose DMEM culture medium containing 60 mg/dL glucose or a high-glucose DMEM culture medium containing 360 mg/dL of glucose in the presence of 5% $CO_2$ at 37° C. for one hour. Thereafter, centrifugation was performed at 2000 g for 10 seconds, the supernatant was collected, and the concentration of insulin was measured. The insulin concentration was measured using the Mouse Insulin ELISA Kit (#10-1247-01) available from Mecordia AB. FIG. 5 shows the results.

The results shown in FIG. 5 indicate that an islet covered with adipose tissue-derived stem cells (composite graft) possesses the same level of glucose responsibility as the mouse transplanted islets alone. Furthermore, the islets that were cultured alone exhibited a morphological change (blackenng) characteristic of apoptosis when 2 days had passed from the start of culturing, and the cells constituting islets began to collapse. In contrast, an islet covered with adipose tissue-derived stem cells (composite graft) maintained their form as shown in the lower right picture of FIG. 4 even when 6 days had passed from the start of culturing, and it was confirmed that apoptosis did not occur. From the facts described above, by culturing islets in the presence of adipose tissue-derived stem cells (in particular, by coating islets with adipose tissue-derived stem cells), it was confirmed that the survival of cells constituting islets can be maintained.

The invention claimed is:

1. A pharmaceutical composition comprising a composite consisting essentially of adipose tissue-derived stem cells adhered onto a pancreatic islet and a pharmaceutically acceptable carrier, wherein 90% or more of the surface of the pancreatic islet is covered with the adipose tissue-derived stem cells.

2. The pharmaceutical composition according to claim 1, wherein the pancreatic islet is covered with the adipose tissue-derived stem cells.

3. The pharmaceutical composition of claim 1, wherein the adipose tissue-derived stem cells are directly adhered to the pancreatic islet.

4. The pharmaceutical composition of claim 1, wherein substantially the entire surface of the pancreatic islet is covered with the adipose tissue-derived stem cells.

5. A method for producing the composite of claim 1, the method consisting essentially of co-culturing of the adipose tissue-derived stem cells and the pancreatic islets.

6. A therapeutic method for diabetes, comprising administration of the pharmaceutical composition of claim 1 to a patient in need of a treatment of diabetes.

* * * * *